United States Patent
Pacetti (10) Patent No.: US 6,663,664 B1
(45) Date of Patent: Dec. 16, 2003

(54) SELF-EXPANDING STENT WITH TIME VARIABLE RADIAL FORCE

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 247 days.

(21) Appl. No.: 09/697,894

(22) Filed: Oct. 26, 2000

(51) Int. Cl.⁷ .................................................. A61F 2/06
(52) U.S. Cl. ...................................... 623/1.2; 623/1.15
(58) Field of Search ............................. 623/1.15, 1.2, 623/1.32, 1.42, 1.43, 1.44, 1.46, 1.38

(56) References Cited

U.S. PATENT DOCUMENTS

| | | | |
|---|---|---|---|
| 5,693,085 A | * 12/1997 | Buirge et al. | ............... 606/192 |
| 5,922,020 A | 7/1999 | Klein et al. | |
| 6,350,277 B1 | * 2/2002 | Kocur | ........................ 623/1.11 |
| 6,379,379 B1 | * 4/2002 | Wang | ......................... 623/1.15 |
| 6,428,569 B1 | * 8/2002 | Brown | ....................... 623/1.15 |

* cited by examiner

*Primary Examiner*—Corrine McDermott
*Assistant Examiner*—William H. Matthews
(74) *Attorney, Agent, or Firm*—Fulwider Patton Lee & Utecht, LLP (57) ABSTRACT

A stent including a network of struts constructed to form a structural member. The struts are configured with undulations having flexible segments that bend to move the structural member from a collapsed or delivery position to an expanded position. A biodegradable material is associated with the flexible segments of the stent struts to change the bending characteristics of the segments and, thus, alter the amount of contraction and expansion exhibited by the stent. The biodegradable material is selected to degrade under certain biological conditions over time so as to vary the resistance to movement effect of the material on the flexible segments of the struts.

20 Claims, 6 Drawing Sheets

SELF-EXPANDING STENT WITH TIME VARIABLE RADIAL FORCE

BACKGROUND OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the outcome of the procedure and reduce the possibility of restenosis.

Stents are generally cylindrically shaped devices which function to hold open, and sometimes expand, a segment of a blood vessel or other arterial lumen, such as a coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted in a compressed state for deployment into a body lumen.

One of the difficulties with prior art stents involves restenosis, which is recurrent stenosis, or narrowing, in a body lumen after a corrective procedure. Restenosis is a multifactorial problem believed to be caused by stimulatory processes stemming from the presence of thrombus, a foreign body reaction to the stent, and stent injury to the endothelium and lumen wall from deployment and the stent's pressure against the lumen wall. A related difficulty for prior art stents involves use in connection with intercoronary brachytherapy. Brachytherapy is traditionally a procedure for treatment of cancer, or other proliferative diseases and the like, wherein radiation is used at or near the target site within the body. The radiation has an antiproliferative effect, meaning that rapidly dividing cells are affected most by the DNA damage induced by the radiation, which leads to apoptosis, or cell death, upon division. Thus, brachytherapy has the positive effect of potentially reducing restenosis after angioplasty or stenting, but it also presents new challenges for prior art stents.

Due to cellular damage and inhibition resulting from brachytherapy, a phenomenon known as positive vessel remodeling has been observed in vivo, which vessel lumen enlargement and, sometimes, medial thinning. Positive remodeling is beneficial to the extent that the vessel is still fully functional. The typical balloon expandable, prior art stent, because of its constant size after expansion, may either prevent positive remodeling from occurring or may be left exposed in the lumen after the lumen wall recedes. Such an exposed stent greatly increases the risk of thrombosis.

Due to the cellular damage and death resulting from brachytherapy, a phenomenon known as positive vessel remodeling has been observed in vivo, where new cells eventually grow and "remodel" the body lumen walls. The typical prior art stent, because of its constant radial expansion and force, may either prevent the positive remodeling from occurring or may be left exposed in the lumen after the lumen wall recedes.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or super-elastic nickel-titanum (NiTi) alloys, which will automatically expand from a compressed state when the stent is advanced out of the distal end of the delivery catheter into the blood vessel. Stents manufactured from expandable heat sensitive materials usually allow for phase transformations of the material to occur, resulting in the expansion and contraction of the stent. Other self-expanding stents may use SIM alloys to allow the stent to move between contracted and expanded positions.

Typical stent delivery systems for implanting self-expanding stents at the target site include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition.

Balloon expandable stents have the advantage of a high radial strength that is capable of holding open a tight stenosis. This stenosis is initially expanded by the force of a high pressure balloon. However, such a stent requires this dilitation to occur all at once. There is the alternative of simply deploying a self-expanding stent, and allowing the lumen to be slowly dilated over time to produce less injury. High levels of vessel injury are directly correlated with the greater levels of restenosis. However, a traditional manner of utilizing self-expanding stents requires predilating the lesion with a balloon, deploying the stent, and then postdilating the stent with another balloon. These many manipulations in the lesion increase the amount of vessel injury and endothelial denudation. Compared to this, the single step of deploying the self-expanding stent is attractive if the acute outcome is acceptable. The other issue, already mentioned, regarding balloon expandable stents is that if positive remodeling occurs, the stent is left exposed in the vessel. These two aspects, the ability to gradually expand the lesion over time, and expand with the vessel in a more passive sense, are compelling reasons to consider self-expanding stents over balloon expandable stents, particularly when used in conjunction with brachytherapy. Use of self-expanding stents to either hold open a previously tight stenosis, or to start the process of opening a lesion without completing predilatation, can require a high initial radial force. Compared to balloon expandable stents, usually of 316L stainless steel, achieving a high initial radial strength with NiTi alloys can be more of a challenge.

Currently, a high initial radial force for a self-expanding stent is accomplished by either oversizing the stent (to increase the strength) or by placing more metal in the stent (i.e., by making the struts thicker and wider). However, oversizing may lead to excessive vessel injury as the stent continues to exert a force against the vessel wall once implanted. For this reason, there is currently a concern that oversizing the stent by a large amount, in order to exert a large initial force, may be detrimental, as the stent will keep pushing the vessel wall possibly causing injury. Moreover, oversizing or increasing the amount of metal in the stent changes the way in which the stent functions biologically. For example, increasing the amount of metal results in a stent having thicker struts and increases the stent to artery ratio, which may not be desirable for every stent application. The stent to artery ratio is defined as the percentage of the vessel wall area covered by the stent struts. With balloon expandable stents, there is a known and preferred range of stent to artery ratio, strut thickness and width. When engineering a self-expanding stent, one challenge is designing a stent which expands to a final diameter, as dictated by the reference vessel size of the body lumen in which the stent is to be implanted, while exerting a radial force at this final diameter that is not injurious to the body lumen wall.

What has been needed and heretofore unavailable is a self-expanding stent that has a time variable radial force. In one configuration, when first deployed, such a stent should exert the necessary force to expand against the lesion, dissected arterial lining, thrombus, embolus, or other lumen abnormality and maintain the patency of the lumen. This process can occur actively, or over a short interval of time. Later, when the vessel wall is remodeling, or simply because the vessel has reached its optimum size, the stent should exert a relatively lower force on the wall, thereby minimizing the risk of injury and allowing more complete repair and healing of the lumen. In a second configuration, the stent should exert a lower radial force when first deployed, this force increasing at a later time. This will facilitate deployment of a self-expanding stent as the stent expansion forces increase the friction against a restraining sleeve or sheath. This configuration is also beneficial when the body lumen is in need of only minor repair and aggressive expansion is not initially desired. The present inventions disclosed herein satisfy these and other needs.

SUMMARY OF THE INVENTION

The present invention is directed to a self-expanding stent having a configuration which allows the radial force exerted by the stent to vary with time. The stent is comprised of a network of resilient struts configured with undulations defining flexible segments which are interconnected to cooperatively form the flexible stent. The flexible segments are bendable to allow the stent to move between its collapsed and expanded positions. Biodegradable material is strategically incorporated into the strut pattern (via the flexible segments) to either encourage or restrict bending or flexing of the flexible segments toward their preferred positions. As the biodegradable material degrades over time, its effect of producing either an increase or decrease of the rate of radial expansion of the stent is gradually lessened.

In one aspect of the present invention, the stent is comprised of struts that have flexible segments which include peaks and valleys that aid in the even distribution of radial expansion forces. The various flexible segments can have, inter alia, U, V, Y and W shapes which bend and flex to allow the composite stent device to expand from its collapsed position. Each of these particular flexible segments includes at least one strut junction where the struts forming the flexible segment meet. The bending or flexing of the strut junctions provides the outward radial force which is developed by the stent to move between its collapsed position to the expanded position. Biodegradable material, which acts as a bend control member, can be strategically placed, for example, within the strut junction of the flexible segment to directly influence the amount of radial force that will be exerted by that particular flexible segment. The amount of radial force exerted by the flexible segment will change once the biodegradable material begins to erode. For example, biodegradable material can be placed within select strut junctions when the stent is in its fully opened, relaxed shape or, alternately, when it is expanded beyond its fully opened and relaxed shape. When the stent is crimped down to its collapsed position, the strut junctions will be placed under greater stress with the biodegradable material in place than they would without the presence of the material. When implanted, the stent exerts a high initial radial strength since the biodegradable material has been placed in compression within the strut junctions and is exerting additional outward force on the struts to increase the overall outward radial force of the composite stent. This radial force drops somewhat as the stent expands further, and then, after the stent is placed in the body vessel, the biodegradable material will gradually degrade. This erosion of the biodegradable material gradually reduces the resistance of the flexible segment to bending and, correspondingly, the amount of radial force exerted by the stent against the lumen wall.

In another aspect of the present invention, the biodegradable material is selectively incorporated into the stent pattern under tension. In this aspect, the radial force generated by the deployed stent would be initially lower than it normally would be without the presence of the biodegradable material and would increase to its full radial strength after the material begins to biodegrade. Depending upon the structure of the struts, the biodegradable material can be placed directly on existing struts at strut junctions or on specially created structures formed on the flexible segments which are adapted to receive the biodegradable material. A number of different structures can be incorporated into a strut pattern to create these regions where the biodegradable material can be applied to help control the amount of bend exerted at the strut junctions to obtain the desired radial force over time characteristics for that particular stent.

In another aspect of the invention, the straight portions of the struts can be formed with decreased cross-sectional areas (strut width) at certain locations which will result in these struts producing less radial force due to the added flexing of the struts at these locations. For example, a slot can be cut into the straight struts and filled with biodegradable material to produce an initial high radial force when the stent is initially implanted in the patient's vasculature. In this manner, the biodegradable material acts to initially stiffen the strut against bending in the region where the strut has a reduced cross-sectional area. Since these regions are under a sheer moment, as the biodegradable material erodes, the struts will have greater flexibility due to the reduced cross-section of the strut, thus lowering the composite radial expansion force exerted by the stent. Using this technique, a large initial radial force can be imparted by the stent which will gradually decrease as the biodegradable material erodes within the patient's vasculature since certain struts become narrower and flex to a greater extent.

In still another aspect of the present invention, one or more filaments of biodegradable material that forms a hoop can be utilized to encircle the entire stent. The filament(s) would expand with the stent and would be left in place within the patient's vasculature. The filament(s) would be placed on the stent in tension thus initially reducing the amount of radial expansion force exerted by the stent. As the filament(s) begins to degrade, the tension placed on the stent decreases which, in turn, allows the stent to deploy to its fully expanded position, and increases the radial force imparted by the stent against the body vessel.

The present invention is also directed to a method of making a self-expanding stent with integrated biodegradable material. The method includes forming the stent pattern and selectively placing the biodegradable material into the strut junctions or reduced strut regions using a solution coating technique. Alternatively, the biodegradable material can be deposited using a manual or automated process.

The present invention is intended for use with any self-expanding stent. This includes stents for the coronary, carotid, neurological, renal, hepatic, iliac, biliary, popliteal, prostrate, femoral or other peripheral vasculature. The stent itself can be made from any of the materials that are used to manufacture self-expanding stents, including, but not limited to, nitinol, elgiloy, and other shape-memory metals. There are no limitations on the stent length or diameter, strut thickness, strut width, or strut pattern of the stent. Variable amounts of biodegradable materials may be used and there are no minimal or maximum amounts that need to be incorporated into the stent. Additionally, more than one type of biodegradable material can be incorporated into the stent.

The stent of the present invention is particularly useful for implantation in body lumens known to have stenotic lesions, dissected arterial linings, thrombus, embolic deposits or other abnormalities because the higher initial radial expansion force can move the tissue and maintain the patency of the lumen. Then, when the biodegradable material has become resorbed, the decreased radial expansion force of the stent, again achieved due to the degradation of the biodegradable material incorporated in the stent structure, helps enable the lumen wall to remodel, or repair itself, to remain healthy, and to hopefully avoid restenosis.

Alternatively, the stent of the present invention can be configured to have a lower initial radial expansion force that gradually or rapidly increases. A lower initial expansion force can facilitate stent deployment from a restraining sleeve. This configuration is also advantageous when the body lumen is in need of minor repair and a high initial radial expansion force is not initially desired. These and other advantages of the present invention become more apparent from the following detailed description of the invention, when taken in conjunction with the accompanying exemplary drawings.

DETAILED DESCRIPTION OF THE PREFERRED EMBODIMENTS

The present invention is directed to a self-expanding stent that has biodegradable bend control members incorporated therein for the purpose of causing the radial force of the stent to vary with time.

Figure 1:
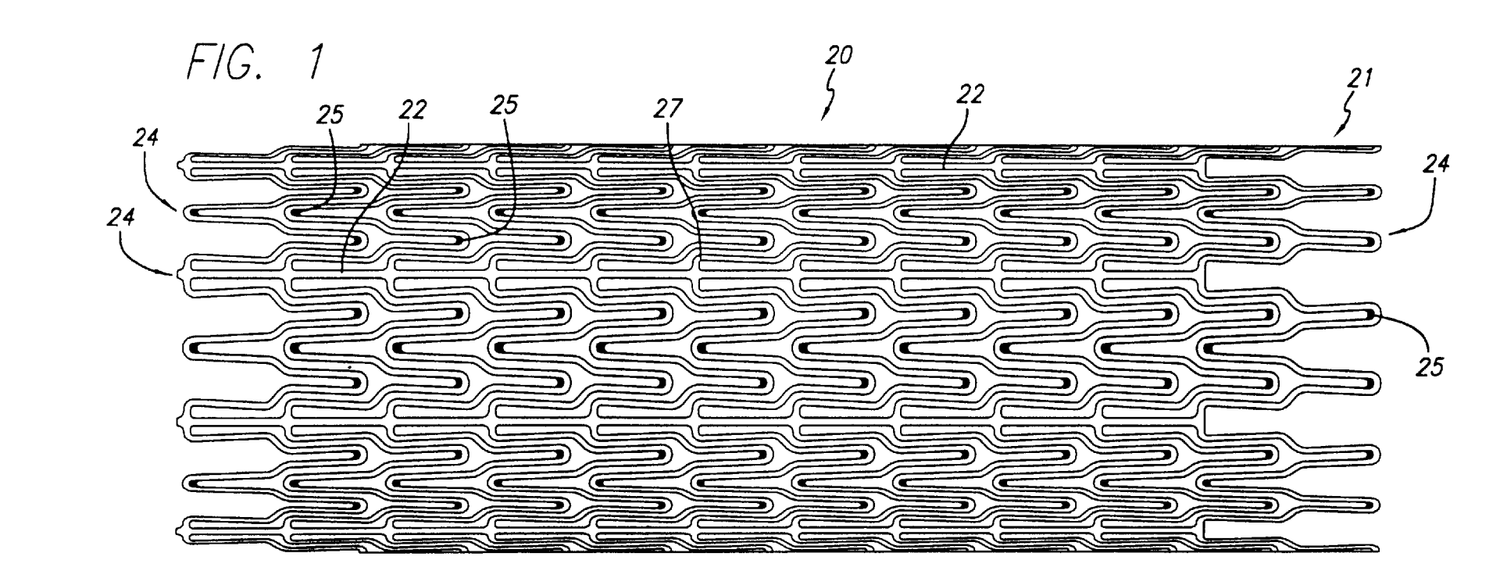
FIG. 1 is a plan view of a flattened self-expanding variable force stent embodying features of the present invention.
Figure 2:
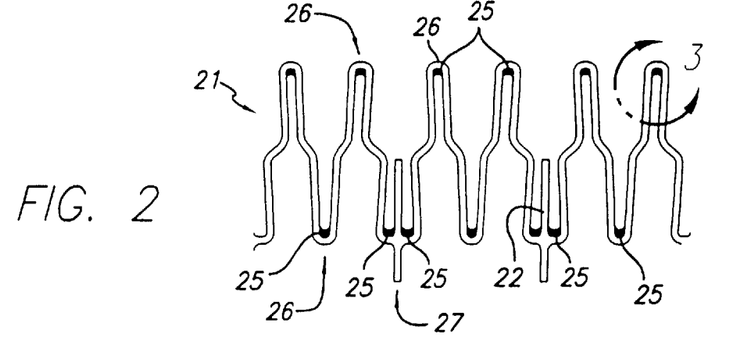
FIG. 2 is a partial view depicting one cylindrical element or ring of the stent shown in FIG. 1.
Figures 3, 4, 5:
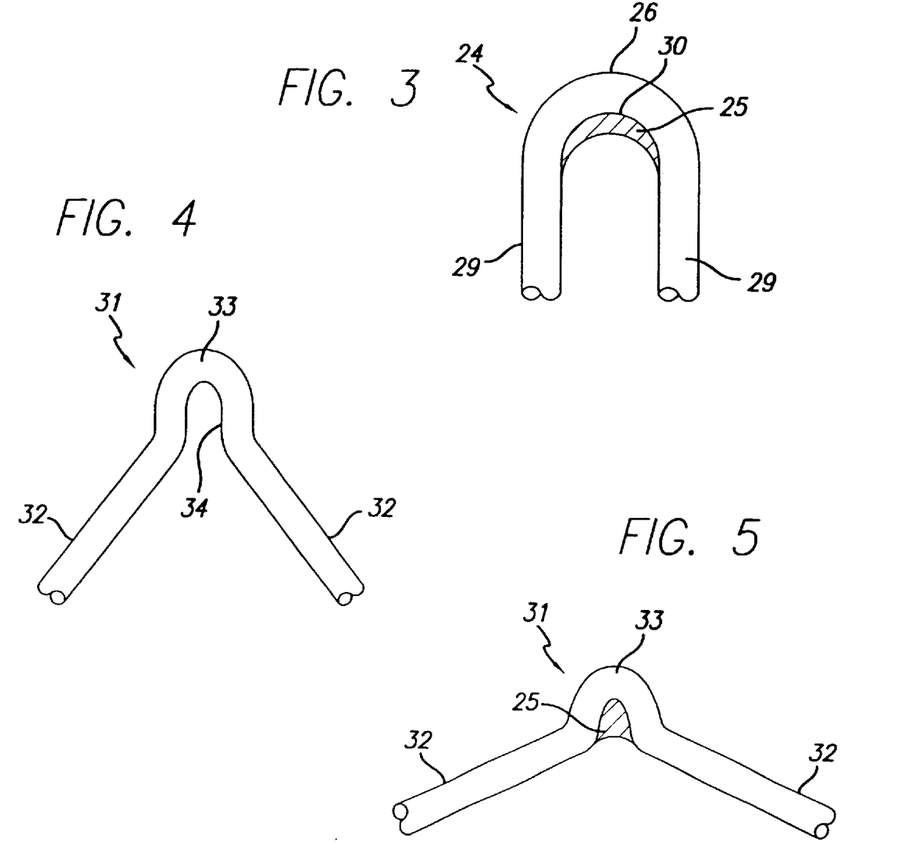
FIG. 3 is an enlarged fragmentary view of one flexible segment from the stent shown in FIG. 1.
FIG. 4 is an enlarged fragmentary view of a modification of a flexible segment in its preferential, or unstressed, configuration without the incorporation of a biodegradable bend control member.
FIG. 5 is a fragmentary view of the segment of FIG. 4 illustrating the flexible segment in an overexpanded state with the incorporation of a biodegradable bend control member.

Referring now to the drawing in which reference numerals represent like or corresponding elements across the drawings, and particularly FIGS. 1–3, there is generally shown a particular embodiment of a self-expanding stent which can be made in accordance with the present invention.

The stent 20 is shown flattened in FIG. 1 to better illustrate the network of struts which cooperate to form the stent 20. It should be appreciated that the struts are normally arranged in a cylindrical configuration to form the generally cylindrically-shaped stent which is implanted in a patient's vasculature to help hold and maintain open a particular body vessel and to prevent restenosis from occurring in the area of treatment. In the embodiment of FIGS. 1–3, the stent 20 typically is comprised of a plurality of radially expandable cylindrical elements 21 disposed generally coaxially and interconnected by elements 22 disposed between adjacent cylindrical elements 21. FIG. 2 shows one particular cylindrical element or ring of the stent of FIG. 1 and the continuous pattern of undulations which include flexible segments 24 which are bendable to allow the stent 20 to move between its collapsed and expanded positions. Each radially expandable cylindrical element 21 of the stent 20 may be independently expanded. Moreover, the shape of the stent can be other than cylindrical, e.g., tapered, to facilitate implantation of the stent into a variety of body lumen shapes.

Biodegradable material defining bend control members 25 selectively control the bending of the flexible segments 24, thereby altering the radially expansion characteristics of the stent. Further, as stent control members 25 degrade under various biological conditions, the resistance to bending of the flexible segments 24 is thereby altered.

As best observed in FIGS. 1 and 2, each cylindrical element 21 includes a number of different flexible segments 24 which are utilized to allow the stent 20 to move between its expanded and collapsed positions. The flexible segments are specifically shown as a plurality of U-shaped flexible segments 26 and W-shaped flexible segments 27, each having a different radius so that expansion forces are more easily distributed over the various segments. In use, the U-shaped flexible segments 26 and W-shaped segments 27 flex or bend to allow each cylindrical element 21 to expand from a collapsed position to an expanded position. It should be appreciated that the present invention can be used to create stents which do not incorporate cylindrical elements or rings as described herein, but rather, other structural elements, such as zigzag patterns, spiral patterns, and the like to create a composite stenting device with time variable radial force. Moreover, the shape of the flexible segments 24 is not limited to U-shaped flexible segments 26 or W-shaped flexible segments 27, as shown in FIGS. 1 and 2, but rather, can include Y-shaped flexible segments, V-shaped flexible segments 31 (shown in FIGS. 4–6), and the like.

Referring now particularly to FIG. 3, the U-shaped flexible segment 26 is shown having two spaced-apart, substantially parallel strut legs 29 joined at a U-bend which forms a strut junction 30 which allows the pair of strut legs 29 to bend or flex. As is shown in the embodiment of FIG. 3, a biodegradable bend control member 25 in the form of a web is mounted in the strut junction 30 to cooperate with the pair of strut legs 29 in controlling the bending or flexing of the U-shaped flexible segment 26. The bend control member 25 can be configured so that it is in compression to urge the pair of strut legs 29 to spread apart relative to the equilibrium position when the purpose of the self-expanding stent 20 is to produce a higher initial radial force of expansion that will decrease with time.

In the alternative, the bend control member 25 can be configured so that it is in tension and urges the strut legs 29 to move closer together relative to the equilibrium position, as when the purpose of such member is to initially restrain the pre-stressed stent from expanding, thus increasing the radial expansion force with time. This configuration may be appropriate, for example, when the body lumen into which the stent 20 is placed is in need of minor repair. Configuring the bend control member 25 in tension also serves the purpose of retaining the strut legs 29 in a compressed condition in order to facilitate delivery of the stent 20 to the target site.

Figure 9:
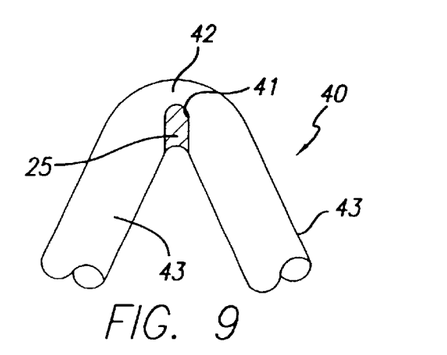
FIG. 9 is a fragmentary view of a modified flexible segment of an embodiment of the self-expanding variable force stent of the present invention.
Figure 10:
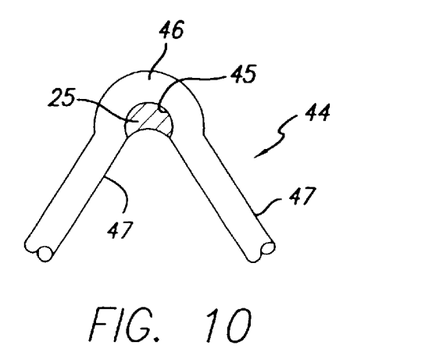
FIG. 10 is a fragmentary view of a modified flexible segment of an embodiment of the self-expanding variable force stent of the present invention.
Figure 11:
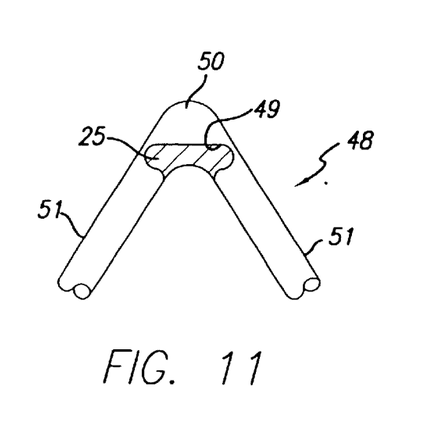
FIG. 11 is a fragmentary view of a modified flexible segment of an embodiment of the self-expanding variable force stent of the present invention.

The self-expanding stent 20 has a preferential, or unstressed, configuration, an assembly configuration wherein the biodegradable bend control member 25 is incorporated into the stent 20, and a delivery, or stressed, configuration. In the embodiment shown in FIGS. 4–6, a substantially V-shaped flexible segment 31 includes a pair of strut legs 32 joined at a strut junction 33. A bend control member 25 in the form of a biodegradable material is placed at the strut junction 33 to control the bending of this substantially V-shaped flexible segment 31. The V-shaped flexible segment 31 is shown in FIG. 4 in its preferential, or unstressed, configuration. The strut junctions 33 of this particular V-shaped flexible segment 31 is somewhat modified to include a notch 34 which provides a larger region for the biodegradable material (bend control member 25) to be deposited. Various shaped notches having various sizes can be utilized in conjunction with this V-shaped flexible segment 31, or any shaped flexible segment, as are shown in FIGS. 9–11. It should be appreciated also that notches could also be formed on the other flexible segment regardless of whether the segment is V-shaped, U-shaped, W-shaped or Y-shaped. Additionally, the size and shape of the notch can be varied with any of these above-identified shapes, along with any other particular shape that may be utilized to form the flexible segment.

Figure 6:
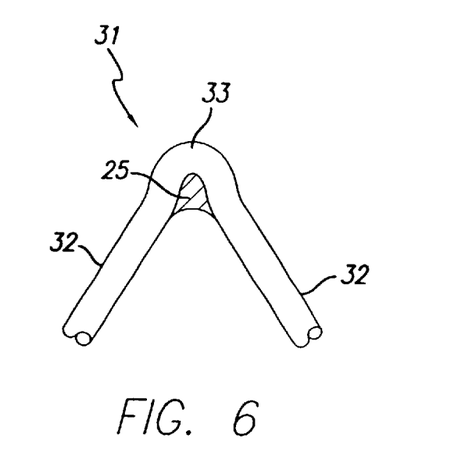
FIG. 6 is a fragmentary view of the segment of FIG. 5 illustrating the flexible segment in its compressed delivery configuration.

The V-shaped flexible segment 31 is shown in its assembly configuration in FIG. 5, with the strut legs 32 flexed to be spread apart relative to one another. In this configuration of the V-shaped flexible segment 31, the biodegradable bend control device 30 is shown installed as a web in the notch 34 formed at the strut junction to control the amount of bending force developed by these strut legs 32. Referring now to FIG. 6, the strut legs 32 are compressed together relative to the position shown in FIG. 5, with the biodegradable bend control member 25 under compression to create greater force for strut legs 32 to expand away from each other.

When the self-expanding stent is to be delivered to a target site in a body lumen, the stent is typically compressed to a low-profile configuration to be held on a delivery catheter, with an outer restraining sheath disposed about its circumference to maintain it compressed until it is ready to be deployed. As the stent is compressed, the free ends of the strut legs 32 are drawn together as shown in FIG. 6. The stent, and thus the V-shaped flexible segment 31, may even be compressed for delivery to the extent that the angle between the strut legs 32 is less than the case for the unflexed stent. In the delivery configuration of FIG. 6, the bend control member 25 is under compression, thereby cooperating with the flexible segment 31 in initially exerting a higher radial expansion force then would be exerted in the absence of the bend control member 25.

It should be appreciated by those skilled in the art that, in operation, when the self-expanding stent of the present invention is released in the patient's body lumen, the biodegradable bend control member 25 will, acting as a brace between the strut legs 32, cooperate in urging the free extremities of such legs laterally apart in the circumferential direction around the wall of the stent. The respective undulations in the stent thus cooperate to maintain radially outwardly acting forces on the wall formed by the undulations to thus maintain the body lumen in an expanded open position properly dilated to the desired size.

It will be further appreciated that the biodegradable material of the bend control member 25 may be selected and configured so as to cooperate in maintaining the stent in the desired expanded configuration for a desired period of time. Degradation of the biodegradable material of the bend control member 25 typically will progressively diminish leading to a reduction of the bracing effect on the strut legs 32.

The tendency of the body lumen to compress the diameter of the stent inwardly will generally be resisted by the resiliency of the undulations as dictated by the struts of the flexible segments under the bracing force of the material in the bend control member. To this end, it will be appreciated by those skilled in the art that the radially inwardly force applied by the wall of the body lumen will apply a force to the relatively free ends of the strut legs thus creating a moment about the strut junction. This moment is resisted by the bracing force of the bend control member in cooperation with the strut legs and the strut junction. As the biodegradable material of the bend control member continues to degrade, the resistive moment applied to the strut legs will progressively diminish, thus freeing the flexible segments defined by such legs and the strut junction to flex, thereby cooperating to somewhat diminish the overall diameter of the stent and allowing the diameter to progressively diminish in profile. After a predetermined time, such as four months or the like, the material of the bend control member will be totally degraded, thus leaving the strut junction to act by itself as a living hinge, resulting in the undulations roughly assuming their preferential position and, consequently, the unstressed profile of the stent itself.

The self-expanding stent of the present invention may be delivered to the target site within a body lumen in typical fashion by being compressed onto the distal end of a delivery catheter and held in place by a restraining sheath. When the catheter has been advanced within the body lumen to the place where the stent is adjacent the target site, the restraining sheath may be withdrawn to deploy the stent, freeing it to expand against the lumen wall. In the embodiment illustrated in FIGS. 4–6, the initial radial expansion force exerted against the lumen wall is relatively high due to the urging of the bend control member. This initial expansion is useful to expand against a lesion, dissected arterial wall, thrombus, embolus or other abnormality and maintain the patency within the body lumen.

As the lumen abnormality is progressively corrected through cellular remodeling over time, the radial expansion force exerted by the stent will gradually decrease as dictated by the amount and type of biodegradable material initially applied. For example, the bend control member can be constructed to fully degrade in about four months time. The parent structure of the stent will remain in place within the lumen, exerting a radial force significantly less than the initial radial expansion force when the stent was deployed, but sufficient to maintain the patency of the lumen and to keep the stent in position. Therefore, a self-expanding stent made in accordance with the present invention will optimally exert an initial force necessary to expand against and open a body lumen, while exerting a lower force later, thereby minimizing the possibility of injury to the lumen wall.

A number of biodegradable materials are currently available for use in the stent of the present invention. One property consistent among most such materials is that the tensile strength is much less than that of metals. It is therefore desirable that the biodegradable bend control members be configured in a way that they function under compression within the stent, as is described above. The table below provides reference data for various biodegradable materials as compared to 316L stainless steel and Nitinol, two materials typically used in stents.

| Material | Max. Tensile Strength (kpsi) | Max. Elong. (%) | Tensile Modulus (Gpa) |
| --- | --- | --- | --- |
| L-polylactide | 12 | 10 | 2.7 |
| D,L-polylactide | 6 | 10 | 2.0 |
| polyglycolide | 10 | 20 | 7.0 |
| polycaprolactone | 5 | 500 | 0.4 |
| 316L (annealed) | 85 | 57 | 200 |
| Nitinol | 130 | 50 | 28–83 |

Biodegradable materials for use in the bend control devices include polyesters, which bulk erode, hydrophobic polyanhydrides, which surface erode from the outside in, and water soluble polymers, which would have to be covalently cross-linked before installation in a stent. A list of appropriate materials includes, but is not limited to, L-polylactic acid, L-polylactide acid, D,L-polylactic acid, polyglycolide, polylactide-coglycolide, polycaprolactone, polytrimethylenecarbonate, polyanhydrides, polyorthoesters, polyphosphazenes, collagens, elastin, fibrin, glycosaminoglycans, hyaluronan, chondroitan sulfate, dextran sulfate, dextran, hydroxyapatite, dahlite, octacalcium phosphate, tricalcium phosphate, β-tricalcium phosphate, brushite, amorphous calcium phosphate, and calcium sulfate. The type and amount of biodegradable material can be selected so as to degrade in the desired time period. Additionally, the biodegradable material may be combined with a therapeutic drug.

The self-expanding stent 20 shown in FIGS. 1–3 may be formed from a metal tube, typically Nitinol, defining the undulations and flexible segments 24 having strut legs 29 which define the outer surface of the stent. The biodegradable bend control member 25 may be deposited within the strut junction between the strut legs 29. In some configurations, the stent itself may be bodily dipped in a biodegradable solution for coating thereof so as to cooperate over the entire extent of the undulations to resist bending. Recesses and confined areas of the stent pattern, which are located at the strut junctions, will tend to retain large amounts of coating solution containing the biodegradable material. It will be appreciated by those skilled in the art that the self-expanding stent of the present invention, and the flexible segments thereof, can be configured in numerous different shapes and configurations and still effectively function to vary the radial expansion of the stent over time. Further, the stent might even flex preferentially from one shape to another, rather than a single shape only changing in scale as the stent flexes. All such variations are a function of the design and construction of the undulations of the self-expanding stent and are within the scope of the present invention.

An alternative method of manufacture involves applying the biodegradable solution to the desired locations within the stent structure by way of an automated microsyringe. As needed for a particular stent design or application, the biodegradable material may be applied to all of the strut junctions or selected ones thereof. An automated microsyringe system would entail mounting the stent on a suitable mandrel or fixture in an unstressed, compressed, or stretched configuration, as required. Once mounted, the stent pattern would initially be registered to provide correct orientation. Then, under computer control, the mandrel would index, thereby moving the stent axially and circumferentially, and the microsyringe would deposit the biodegradable material.

Excess biodegradable material applied to the stent structure can be wiped away using a manual or automated process. Excess coating solution can also be removed by centrifuging the stent axially or lengthwise, by the action of compressed gas directed against the stent, or by a vacuum nozzle held in proximity to the stent while the biodegradable material is still in a liquid state. For some embodiments, it may be desirable to not remove any solution, and, rather, leave the entire stent coated.

The biodegradable material may be affixed within one or more of the strut junctions of the stent in their preferential configurations to thus cooperate with the parent material of such stent to maintain it in such preferential configuration. Then, when the stent is compressed, as to deliver it to a target site within a patient's body lumen, the bend control member, being in compression, will serve to increase the force of initial radial expansion. During manufacture, the stent may be flexed to spread the strut legs of the flexible segment apart from their preferential position and be maintained so flexed as the biodegradable bend control member is applied within one or more of the strut junctions. Thus, when the stent is released from its expanded position, the biodegradable bend control material will, being in a compressed state, serve to resist the tendency of the parent material of the stent to retract to the preferential configuration, thereby maintaining the stent flexed from its preferential position. In other modifications, it is possible during manufacture to flex the strut legs of the flexible segment toward one another while the bend control material is applied to hold the stent flexed to a profile reduced from its preferential position.

Figure 7:
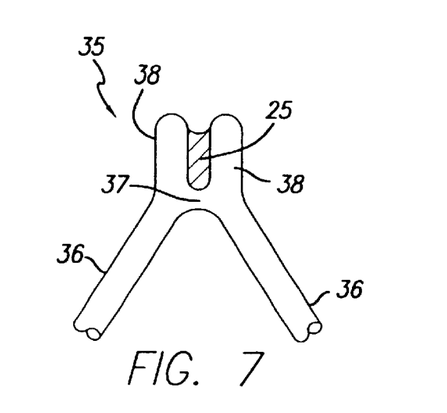
FIG. 7 is a fragmentary view of a flexible segment of a second embodiment of the self-expanding variable force stent of the present invention.

The function of the biodegradable bend control member is also affected by the location within the stent structure wherein the material is placed. Another embodiment of the self-expanding variable force stent of the present invention, as shown in FIG. 7, includes a flexible segment 35 having a substantially V- or a U-shape as has been previously described. This particular flexible segment 35 also includes a pair of strut legs 36 which meet at a strut junction 37. The flexible segment 35 further includes a pair of outwardly projecting fingers or tines 38 which define a gap 39 which receives a web of biodegradable material defining the bend control member 25. This gap 39 is very similar to the notch 34 which is formed on the V-shaped flexible segment 31 shown in FIGS. 4–6. It has large enough region to receive the web of biodegradable material which defines the bend control member 25 in order to control the amount of bend which takes place at the strut junction 37.

Figure 8:
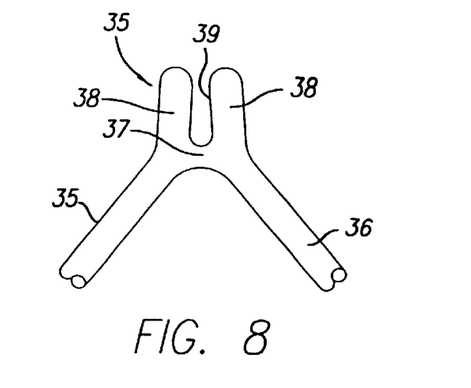
FIG. 8 is a fragmentary view illustrating the flexible segment of FIG. 7 in its preferential configuration without the incorporation of a biodegradable bend control device.

The flexible segment 35 is shown in its preferential, or unstressed, configuration in FIG. 8. During manufacture, the strut legs 36 may be flexed toward one another as shown in FIG. 7, resulting in the free ends of the tines 38 spreading apart as shown. With the strut legs 36 so flexed together, the bend control member 25 may be applied, filling the gap 39 to resist the tines 38 drawing together and thus urging the strut legs 36 to their more contracted position as shown in FIG. 7. In this embodiment, the bend control member 25 is under compression as it resists the tendency of the flexible segment 35 to return to its preferential configuration of FIG. 8, where the legs 36 are spread further apart as compared to the position of the strut legs 36 in the assembly configuration of FIG. 7. Therefore, the bend control member 25 serves to restrain the flexible segment 35 in a relatively compressed, or delivery state.

In the embodiment of FIG. 7, the self-expanding stent of the present invention has the unique ability to exert a relatively low radial expansion force when first deployed, and then exert a higher expansion force later. It will be appreciated by those skilled in the art that, in operation, when the self-expanding stent is released in the patient's body lumen, it will initially expand to a relatively low profile position by the overall cooperation of the biodegradable bend control member that act as a brace between the tines 38 to urge the free extremities of the strut legs 36 laterally together in the circumferential direction around the wall of the stent. In this way, the respective undulations in the stent cooperate to restrain the radial expansion of the wall formed by the undulations to thus provide a relatively low radial expansion force against the wall of the body lumen.

It will be appreciated that the biodegradable material of the bend control member may be selected with characteristics and applied in such quantities as to perform under the conditions of the particular patient so as to allow the radial expansion force of the stent to gradually increase over a desired period of time as the quantity of the biodegradable material and the bracing effect thereof on the tines 38 progressively diminishes. The tendency of the body lumen wall to compress the wall of the stent inwardly will generally be resisted by the resiliency of the undulations as dictated by the strut legs 36 integrally connected to and restrained by the tines 38 braced by the biodegradable bend control member 25 remaining. Thus, the radially inwardly force applied by the wall of the body lumen will apply a force to the relatively free ends of the strut legs 36, creating a moment about the strut junction 37. This moment is resisted by the parent material of the strut legs 36 and the strut junction 37, but is increased by the operation of the bend control member 25 between the tines 38.

As the biodegradable material of the bend control member 25 continues to degrade, the increased moment applied to the strut legs 36 and the strut junction 37 through the bracing of the tines 38 will progressively diminish, thus freeing the undulations defined by the strut legs 36 to increasingly flex outwardly away from one another, thereby cooperating to increase the overall diameter of the stent wall and allowing such wall to progressively increase in profile. After a predetermined time, the material of the bend control member 25 will be totally degraded, thus leaving the strut junction 37 to act by itself as a living hinge, resulting in undulations assuming their preferential configuration and, consequently, the relatively higher profile of the stent itself.

One advantage of this embodiment is that during deployment of the self-expanding stent, the outer restraining sheath can be more easily retracted, as the contact force between the stent and the inside surface of the sheath would be lessened due to the restraining effect of the bend control member 25. Further, the body lumen wall is gradually and less traumatically displaced, which is beneficial when the lumen is in need of only minor repair and allows some degree of fluid communication even prior to the implantation of the stent. It will be appreciated by those skilled in the art that these same advantages can be achieved by affixing a biodegradable bend control device in the strut junction of a flexible segment while it, and the whole stent, is in compression. In this way, the bend control member is in tension, rather than compression, as it restrains the stent from moving toward its preferential expanded configuration.

Another embodiment of the present invention, shown in FIG. 9, includes a substantially bendable V-shaped flexible segment 40, formed with an elongated, open-ended notch 41 at the strut junction 42. A biodegradable web defining the bend control member 25 is mounted in the notch 41. Therefore, the notch 41 serves (1) to provide a seat for the bend control member and (2) to decrease the radial expansion force of the self-expanding stent itself. Decreasing the contribution to the overall radial expansion force by the parent material of the stent offsets, at least in part, the effect of increasing the radial expansion force due to the installation of the bend control member in the notch 41, thereby achieving an overall initial radial expansion force that is relatively lower, and therefore safer for some applications. The flexible segment 40 is somewhat similar to the segment shown in FIGS. 4–6, but lacks the curved "hump" at the strut junction as is shown in FIGS. 4–6. However, the flexible segment operates in the same manner as the embodiment shown in FIGS. 4–6.

It will be appreciated by those skilled in the art that as the biodegradable material of the bend control member degrades, the resistance to flex of the strut legs 43 toward each other will be gradually diminished, thus gradually allowing the undulations and stent wall to assume a lower profile as such legs gradually collapse toward one another. The configuration of the elongated notch 41 serves to dictate that the biodegradable material of the bend control member will degrade progressively inwardly from both strut junction 42, thus providing somewhat of a linear rate of change of the radial expansion force over time. Therefore, the bend control member and the strut cooperate to resist lateral inward flexing of the strut legs 43 to thus provide the desired rate of diminishment in forces tending to hold the undulations and stent wall expanded and to thereby provide for progressive reduction of the stent expansion force. As the material of the bend control member becomes totally degraded, it will be appreciated that only the relatively thin living hinge at the apex of the flexible segment will provide the resistance to collapse and urge the stent toward its preferential configuration. Similar to the embodiment illustrated by FIG. 6, the resultant moment created by the radially inward force of the body lumen will thus be resisted by the relatively minimal cross-section of the parent material in the living hinge at the strut junction.

As shown in FIG. 10, another embodiment of a flexible segment 44 includes a rounded notch 45 formed in the strut junction 46, with a web of biodegradable material defining the bend control member 25 mounted in the notch 45. This creates a circular-shaped hinge which, in cooperation with the semi-circularly shaped biodegradable bend control member in compression, will function, upon initial deployment of the stent, to provide a substantial moment forcing the relatively free extremities of the strut legs 47 laterally outwardly to thus exert forces maintaining the stent in its preferential, relatively large profile.

It will be appreciated that the biodegradable bend control member affords a relatively large surface area of exposure to the degradation effects within the body lumen, and may provide for somewhat accelerated degradation and a more rapid decay in the material of the bend control member, and, consequently, the bracing effect thereof. As the biodegradable material of the bend control member is reduced and diminished, it will be appreciated that the somewhat robust cross-section of the circular hinge will continue to provide substantial resistance to bending and thus continue to provide substantial resistance to radially inwardly collapse of the stent, but without the added resistance of the bend control member.

In yet another embodiment of a flexible segment 48 as shown in FIG. 11, a laterally projecting, generally elliptically shaped notch 49 is formed in the strut junction 50, with a biodegradable bend control member mounted in the notch 49. The bend control member serves as a brace and cooperates with the strut junction 50 to provide substantial resistance to the tendency of the lumen wall to force the undulations toward their diminished size and consequently to radially inwardly collapse the stent. It will be appreciated that the rate of decay of the bend control member is dictated by the characteristics of the material used and the surface exposure thereof. To this end, it will be appreciated that degradation will occur somewhat constantly in the major axis of the bend control member as further influenced by the degradation from the strut junction 50. As the bend control member progressively degrades, the resistance of the strut legs 51 to bending at the opposite ends of such device is to a great degree controlled by the respective hinge 52, thus providing two main areas of flexure. Consequently, as degradation continues, the expansion moment of the strut legs 51 will be further diminished, thus freeing the legs to flex inwardly about the hinge 52, thereby gradually diminishing the radial force generated by the stent.

These multiple notch configurations allow biodegradable webs and braces of varying shape and thickness to be mounted within the stent struts. The variance of these webs and braces, which define the bend control member, affects both the volume and the exposed surface area of the biodegradable material, which, in turn, provides increased, more precise control of the time variable radial expansion of the stent of the present invention.

Figure 12:
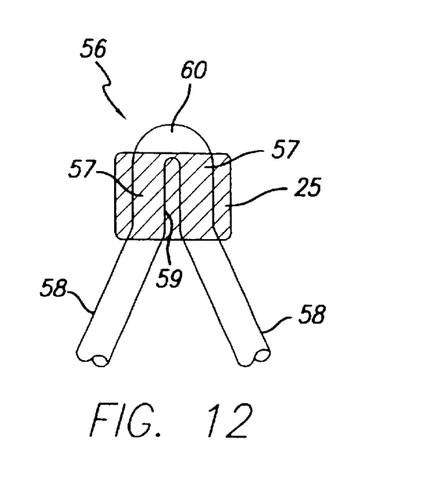
FIG. 12 is a fragmentary view of a modified flexible segment of an embodiment of the self-expanding variable force stent of the present invention.

Referring now to FIG. 12, in another embodiment, much like the embodiment illustrated in FIG. 6, the flexible segment 56 has a somewhat V-shaped configuration which includes a pronounced U-bend 57 which extends away from strut legs 58. This U-bend 57 includes a notched region 59 right at the strut junction 60. However, in the embodiment illustrated by FIG. 12, the biodegradable bend control member 25 is not mounted within the strut junction 60, but rather is in the form of a band that encapsulates the U-bend 57, thereby cooperating to control the movement of strut legs 58.

It will be appreciated by those skilled in the art that the biodegradable bend control member of the embodiment shown in FIG. 12 has a significantly larger surface area exposed to the degradation effects of the body lumen as compared to the exposed surface area of the bend control devices of other embodiments. This feature serves to enable the present embodiment to have a relatively higher rate of change of the radial expansion force, thereby moving the stent from its initial low radial expansion and decreased profile to a higher radial expansion force and larger profile more rapidly. Therefore, this embodiment is yet another means to achieve various radial expansion rates for the stent of the present invention.

Figure 13:
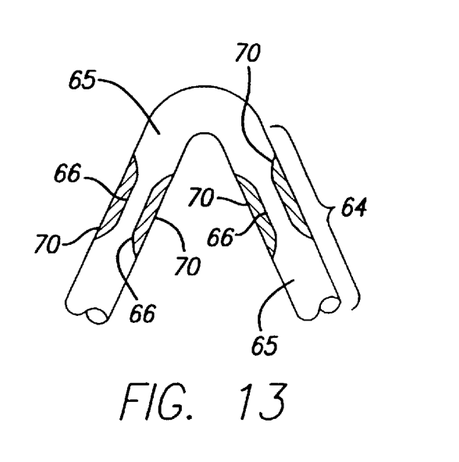
FIG. 13 is a fragmentary view showing a modified bend control member applied to the reduced cross-sectional region of a stent made in accordance with the present invention.

Referring now to FIGS. 13–16, reduced cross-section linear strut segments can also accommodate a biodegradable bend control member in order to initially cooperate in resisting bending of the flexible segments as the self-expanding stent expands within a body lumen. In one embodiment, linear segments 64 within a strut 65, are necked down in a mid-section area, as shown in FIG. 13, such that the cross-section of strut 65 forms a necked-down area 66. The necked-down region 66 is filled with biodegradable material forming the bend control member 70 encapsulating the area and serving to cooperate in providing the linear segments with initial stiffness against bending. In a similar embodiment, illustrated by FIG. 14, longitudinal through-slots 71 are formed within the linear segments 72 of a strut 73. Biodegradable material forming the bend control member 70 within these slots 71, again, to cooperate in initially stiffening the linear segments 72.

Figure 14:
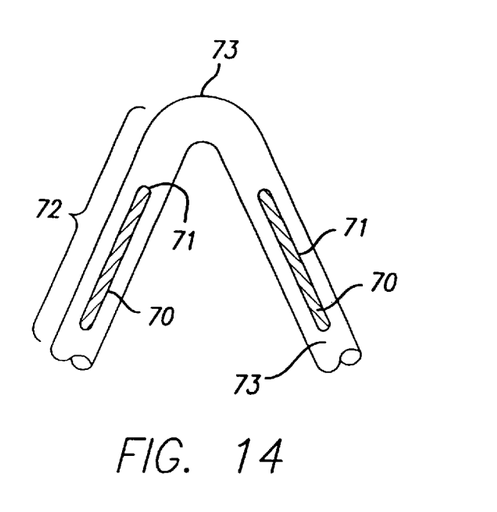
FIG. 14 is a fragmentary view showing a modified bend control member applied to the reduced cross-sectional region of a strut made in accordance with the present invention.

Referring to the embodiments of the present invention shown in FIGS. 13 and 14, it will be appreciated by those skilled in the art that, upon deployment, the strut legs 65 and 73 will cooperate together in causing the undulations to assume respective deployed positions dictated by the flexibility of such legs, as governed by the structure of the respective cross-sections formed by the core of parent material and the biodegradable bend control members 70, respectively, and further dictated by the V-shaped strut junctions. As the bend control member 70 progressively degrades, the resistance to bending afforded by the cooperation of such devices and the corresponding strut parent material cores will diminish. Consequently, the moment applied to expand the lumen wall will thus progressively diminish, thereby reducing the potential for ongoing vessel injury or allowing the stent to be compressed, thereby gradually reducing the profile thereof.

Figure 15:
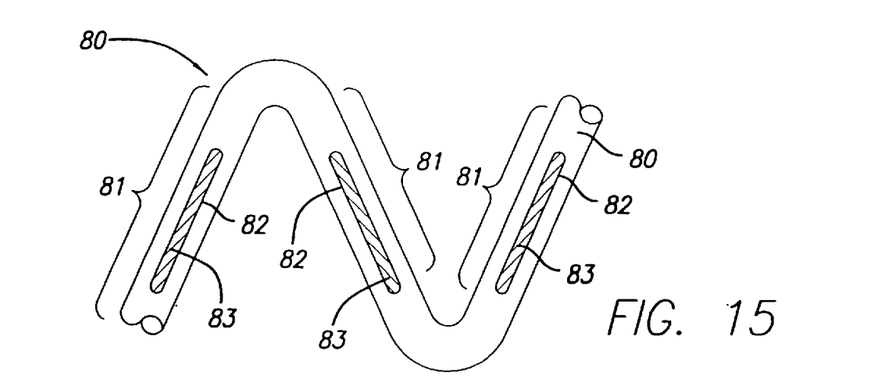
FIG. 15 is a fragmentary view of multiple strut segments with bend control members affixed thereto.

A strut 80 is illustrated in FIG. 15 as having three linear segments 81, each formed with one longitudinal slot 82.

Figure 16:
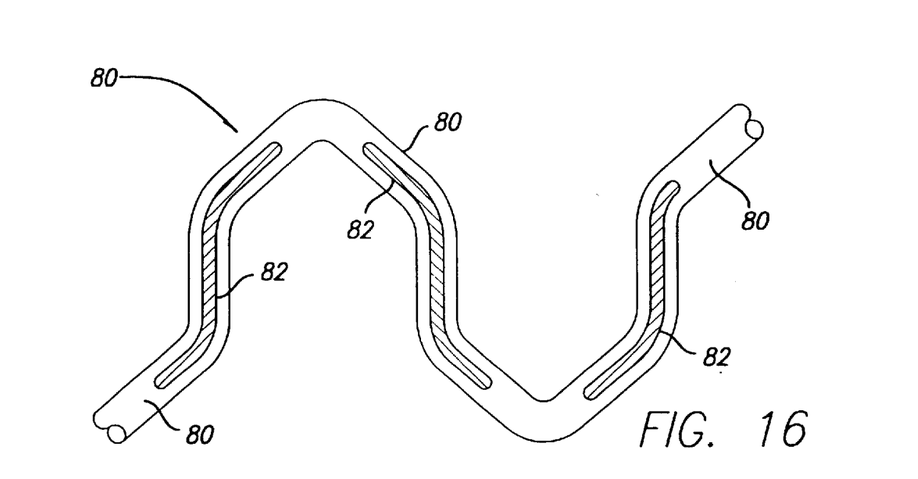
FIG. 16 is a fragmentary view of the multiple strut segments of FIG. 16 showing the bend control members degraded which allows the segments to flex.

Biodegradable material is formed by a bend control member 83 inserted within the respective linear slots. For the purposes of the illustration of FIGS. 15 and 16, the strut 80 is assumed to be part of a self-expanding stent that has been implanted in a body lumen and is presently expanded against the lumen wall. As illustrated by FIG. 16, then, the once-linear segments 81 are flexing under the pressure (somewhat exaggerated for demonstrative purposes) exerted by the lumen wall because the bend control member 83 has now completely eroded, leaving the three longitudinal slots 82 empty so that the segments 81 effectively have a reduced cross-section and are weaker under bending. In this embodiment, the segments 81 will increasingly flex as the biodegradable material of the bend control member 83 erodes, thereby causing the radial expansion force, or the profile of the stent, to decrease with time.

Figure 17:
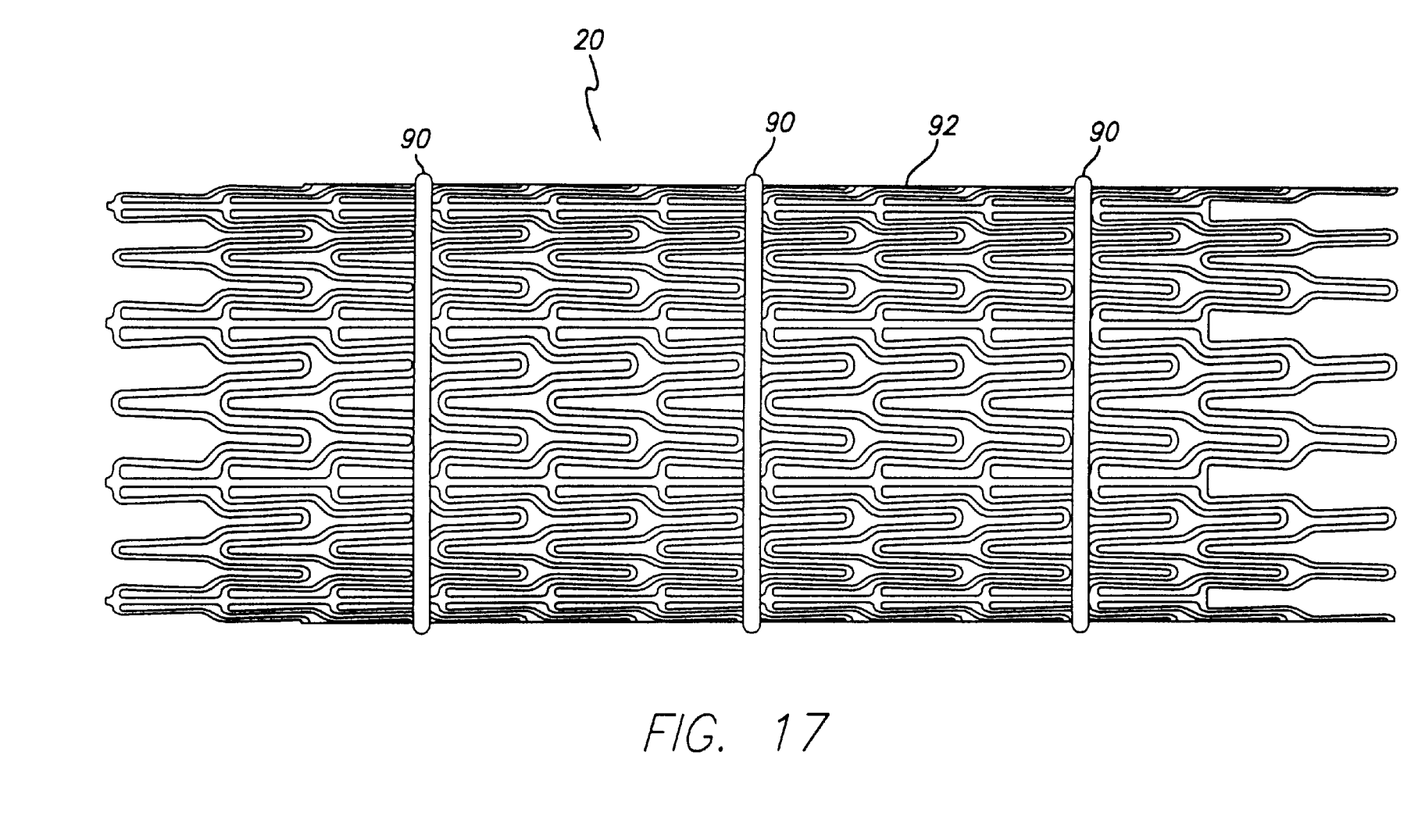
FIG. 17 is a plan view of another embodiment of a self-expanding variable force stent of the present invention.
Figure 18:
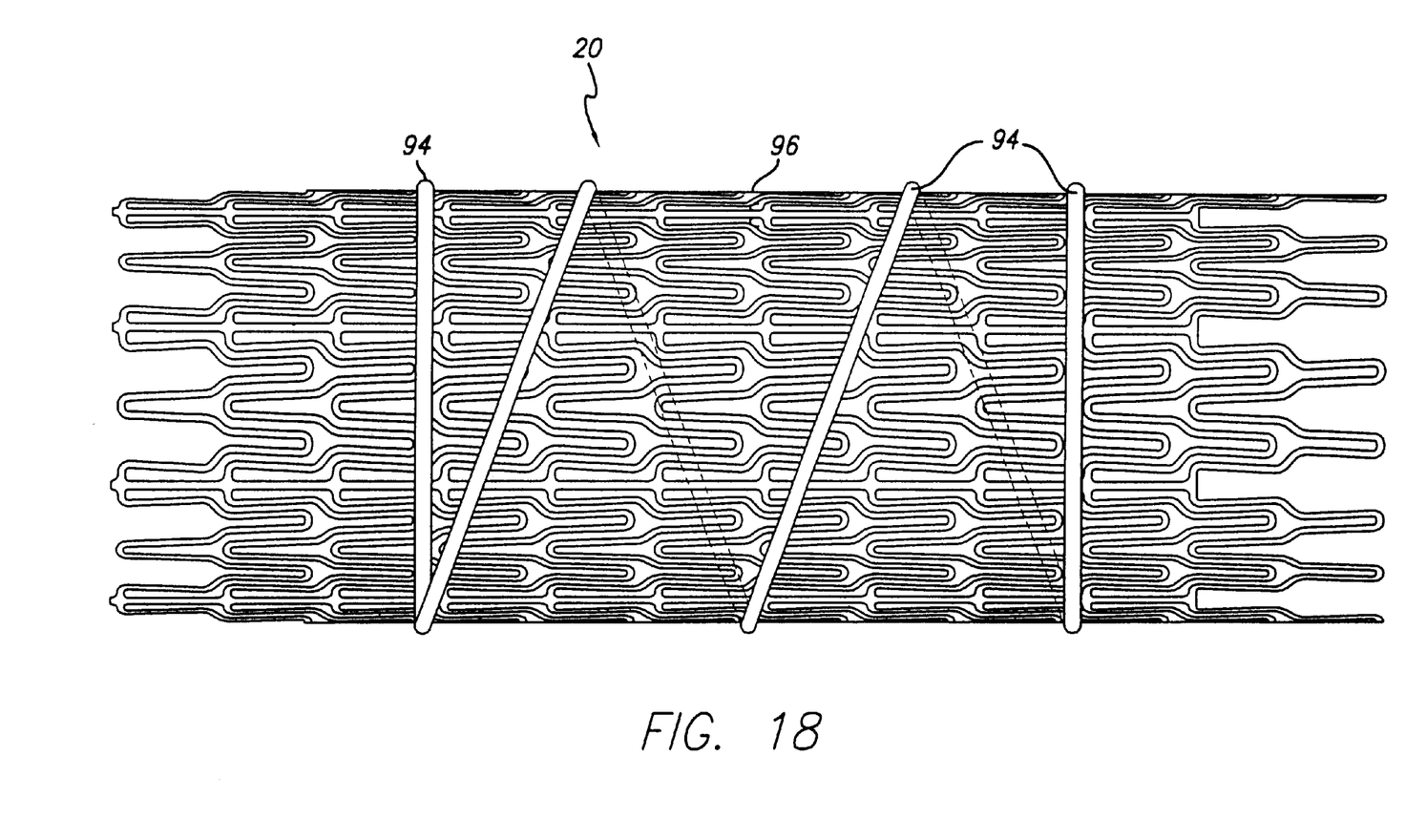
FIG. 18 is a plan view of another embodiment of a self-expanding variable force stent of the present invention.

Other embodiments of the present invention, as shown in FIGS. 17 and 18, include a biodegradable bend control member 90 in the form of a filament that encircles the perimeter of the stent body, thereby initially restraining its radial expansion. As shown in FIG. 17, an embodiment of the present invention is comprised of a biodegradable filament in the form of one or more independent bands that are placed circumferentially about the tubular wall 92 of the stent 20. In a related embodiment, as shown in FIG. 18, the biodegradable filament consists of one continuous helical band 94 about the tubular wall 96 of the stent 20. The bands are placed when the stent is in a compressed condition, thereby causing such bands to initially restrain such stents in a compressed state. Then, as the bands degrade over time and become weaker, the stents will gradually expand radially. Finally, the bands will break or degrade altogether, allowing the stents to unrestrainably expand against the body lumen wall. These embodiments of the present invention serve as additional examples of the means by which biodegradable material can cooperate with a self-expanding stent to vary the radial expansion force and profile characteristics of the stent over time. Further, these embodiments have the added advantage of assuring that the biodegradable material of the bend control device directly contacts the tissue of the body lumen in which the stent is deployed, thereby providing more predictable and rapid degradation.

Since the self-expanding stent of the present invention has the novel feature of a radial expansion force that varies with time, it is particularly well suited for applications where a relatively large initial radial expansion force is required to create patency within a body lumen having a lesion, dissected arterial lining, thrombus, embolus, or other abnormality, for further reducing the likelihood of restenosis, and for use in conjunction with brachytherapy procedures. Further, the stent of the present invention is equally well suited for applications where a low initial radial expansion force is sufficient, as when the body lumen is in need of minor repair. This unique variable radial expansion feature, coupled with the other attributes of prior art self-expanding stents, provides a highly desirable support member for all vessels in the body. Other modifications and improvements may be made without departing from the scope of the invention.

What is claimed is:

1. A self-expanding stent, comprising:
a plurality of struts constructed to form an expandable structural member and configured with undulations having flexible segments bendable to cooperate in expanding the structural member; and
a biodegradable bend control member associated with at least one flexible segment to change the bending characteristics of the flexible segment to which it is associated, wherein the structural member expands to a preferential configuration in the absence of the biodegradable bend control member and the biodegradable bend control member is in compression to urge the flexible segment to move further apart relative to the preferential configuration upon expansion of the structural member.

2. The self-expanding stent of claim 1, further including:
at least another biodegradable bend control member associated with some of the flexible segments.

3. The self-expanding stent of claim 1, wherein:
the biodegradable bend control member is formed of a material selected from the group consisting of polyesters, hydrophobic polyanhydrides, water-soluble polymers, L-polylactic acid, L-polylactide acid, D,L-polylactic acid, polyglycolide, polylactide-coglycolide, polycaprolactone, polytrimethylenecarbonate, polyanhydrides, polyorthoesters, polyphosphazenes, collagens, elastin, fibrin, glycosaminoglycans, hyaluronan, chondroitan sulfate, dextran sulfate, dextran, hydroxyapatite, dahlite, octacalcium phosphate, tricalcium phosphate, β-tricalcium phosphate, brushite, amorphous calcium phosphate, and calcium sulfate.

4. The self-expanding stent of claim 1, wherein:
the biodegradable bend control member is constructed of a material which will degrade in time.

5. The self-expanding stent of claim 4, wherein:
the biodegradable bend control member is selected to degrade in about four months.

6. The self-expanding stent of claim 1, wherein:
the biodegradable bend control member includes a therapeutic drug.

7. A self-expanding stent, comprising:
a plurality of struts constructed to form an expandable structural member and configured with undulations having flexible segments bendable to cooperate in expanding the structural member;
a biodegradable bend control member associated with at least one flexible segment to change the bending characteristics of the flexible segment to which it is associated, at least one of the flexible segments including a pair of strut legs connected at a strut junction; and
the biodegradable bend control member is attached at the strut junction to control the movement of the strut legs relative to one another, wherein the structural member expands to a preferential configuration in the absence of the biodegradable bend control member and the biodegradable bend control member is configured to urge the strut legs to move further apart relative to the preferential configuration upon expansion of the structural member.

8. The self-expanding stent of claim 7, wherein:
the flexible segment is formed with a shape selected from the group consisting of V-shapes, U-shapes, Y-shapes and W-shapes.

9. A self-expanding stent, comprising:
a plurality of struts constructed to form an expandable structural member and configured with undulations having flexible segments bendable to cooperate in expanding the structural member;
a biodegradable bend control member associated with at least one flexible segment to change the bending characteristics of the flexible segment to which it is associated, at least one of the flexible segments including a pair of strut legs connected at a strut junction and a notch formed near the strut junction; and the biodegradable bend control member is placed within this notch to control the movement of the strut legs relative to one another, wherein the structural member expands to a preferential configuration in the absence of the biodegradable bend control member and the biodegradable bend control member is configured to urge the strut legs to move further apart relative to the preferential configuration upon expansion of the structural member.

10. A self-expanding stent, comprising:

a plurality of struts constructed to form an expandable structural member and configured with undulations having flexible segments bendable to cooperate in expanding the structural member;

a plurality of biodegradable bend control member associated with some of the flexible segment to change the bending characteristics of the flexible segment to which it is associated, some of the flexible segments each including a pair of strut legs connected at a strut junction; and the biodegradable bend control members are attached at the strut junctions to control the movement of the strut legs relative to one another, wherein the structural member expands to a preferential configuration in the absence of the biodegradable bend control members and the biodegradable bend control members are configured to urge the strut legs to move further apart relative to the preferential configuration upon expansion of the structural member.

11. The self-expanding stent of claim 10, wherein:

some of the flexible segments are formed with a shape selected from the group consisting of V-shapes, U-shapes, Y-shapes and W-shapes.

12. A self-expanding stent, comprising:

a plurality of resilient undulating struts cooperating to form a flexible structural member, some of the struts being bendable to cause them to develop an outward radial force to move the structural member from a delivery position to an expanded position having a preferential configuration; and at least one biodegradable bend control member associated with at least one of the undulating struts to increase the amount of radial force being developed by the structural member as it moves into the expanded position.

13. The self-expanding stent of claim 12, further including:

at least another biodegradable bend control member associated with at least some of the struts and cooperating therewith to increase the amount of radial force being developed by the structural member as it moves into the expanded position.

14. The self-expanding stent of claim 12, wherein:

at least certain ones of the struts are formed with elongated co-extensive legs configured to flex laterally relative to one another; and the biodegradable bend control members are mounted between these legs.

15. The self-expanding stent of claim 12, the biodegradable bend control member is in compression to urge the struts to expand beyond the preferential configuration.

16. The self-expanding stent of claim 15, wherein:

the biological bend control member is made from a material which will degrade in time to allow the stent structure to move back into the preferential configuration.

17. A self-expanding stent, comprising:

an expandable stent structure expandable from a first diameter configuration to a second diameter configuration; and a biodegradable bend control member associated with the stent structure, the bend control member being adapted to urge the stent structure to expand to a third diameter configuration which is larger than the second diameter configuration, the stent structure expanding only to the second diameter configuration in the absence of the biodegradable bend control member.

18. The self-expanding stent of claim 17, wherein:

the biodegradable bend control member is in compression to urge the stent structure into the third diameter configuration.

19. The self-expanding stent of claim 17, wherein:

the biological bend control member is made from a material which will degrade in time to allow the stent structure to move back into the second diameter configuration.

20. The self-expanding stent of claim 19, further including:

a plurality of biodegradable bend control member associated with the stent structure to urge the stent structure to expand to the third diameter configuration.

* * * * *

UNITED STATES PATENT AND TRADEMARK OFFICE
CERTIFICATE OF CORRECTION

PATENT NO. : 6,663,664 B1
DATED : December 16, 2003
INVENTOR(S) : Stephen D. Pacetti Page 1 of 1

It is certified that error appears in the above-identified patent and that said Letters Patent is hereby corrected as shown below:

Column 16,
Line 56, before "flexible" insert -- at least one --.

Column 17,
Line 47, before "radial force" insert -- outward --.

Column 18,
Line 15, after "claim 12," insert -- wherein --.

Signed and Sealed this

Eighteenth Day of May, 2004

JON W. DUDAS
*Acting Director of the United States Patent and Trademark Office*